(12) United States Patent
Castillo et al.

(10) Patent No.: US 12,239,932 B2
(45) Date of Patent: Mar. 4, 2025

(54) BERNOULLI AIR PROCESSING SYSTEM

(71) Applicant: Purdue Research Foundation, West Lafayette, IN (US)

(72) Inventors: Luciano Castillo, Carmel, IN (US); Ali Doosttalab, West Lafayette, IN (US); Carsten Westergaard, Houston, TX (US); Victor Castano, Queretaro (MX); Ernest Rowland Blatchley, III, West Lafayette, IN (US); Rita Appiah, West Lafayette, IN (US); Helber Antonio Esquivel-Puentes, West Lafayette, IN (US); Abigayle Moser, Ames, IA (US); Jhon Jairo Quinones Cortes, The Hague (NL); Richard M. Voyles, West Lafayette, IN (US); Haoguang Yang, Shenzhen (CN)

(73) Assignee: Purdue Research Foundation, West Lafayette, IN (US)

( * ) Notice: Subject to any disclaimer, the term of this patent is extended or adjusted under 35 U.S.C. 154(b) by 770 days.

(21) Appl. No.: 17/501,663

(22) Filed: Oct. 14, 2021

(65) Prior Publication Data

US 2022/0111323 A1    Apr. 14, 2022

Related U.S. Application Data

(60) Provisional application No. 63/091,860, filed on Oct. 14, 2020.

(51) Int. Cl.
*B01D 46/00* (2022.01)
*A61L 9/20* (2006.01)
(Continued)

(52) U.S. Cl.
CPC .......... *B01D 46/0045* (2013.01); *A61L 9/20* (2013.01); *B01D 46/0028* (2013.01);
(Continued)

(58) Field of Classification Search
None
See application file for complete search history.

(56) References Cited

U.S. PATENT DOCUMENTS 3,710,557 A * 1/1973 Couchman ........... G01N 1/2247
 73/863.03
4,084,918 A * 4/1978 Pavlecka ................ F03D 3/062
 415/4.4

(Continued)

OTHER PUBLICATIONS

Awadalla et al., 3D framework combining CFD and MATLAB techniques for plume source localization research, Building and Environment 70 (2013) 10-19.
(Continued)

*Primary Examiner* — Brit E. Anbacht
(74) *Attorney, Agent, or Firm* — Piroozi-IP, LLC (57) ABSTRACT

An air processing system is disclosed. The system includes a mobile robot, and the robot includes an intake module, the module includes a manifold, a first airfoil disposed on the manifold and configured to allow air of an area designed to have its air cleaned to enter the manifold, a second airfoil disposed one the manifold opposite the first airfoil configured to allow air from the area to enter the manifold, and a collector provided in between the first airfoil and the second airfoil and disposed on the manifold configured to receive air from the manifold and thus filter the air, and the system further includes a controller configured to provide one of remote control and autonomous control of the mobile robot.

24 Claims, 11 Drawing Sheets

(51) Int. Cl.
  *B01D 46/24*   (2006.01)
  *B01D 46/46*   (2006.01)
  *B01D 46/58*   (2022.01)
  *B01D 46/62*   (2022.01)
  *G05D 1/00*    (2024.01)

(52) U.S. Cl.
  CPC ......... *B01D 46/0049* (2013.01); *B01D 46/24* (2013.01); *B01D 46/46* (2013.01); *B01D 46/58* (2022.01); *B01D 46/62* (2022.01); *G05D 1/0011* (2013.01); *G05D 1/0088* (2013.01); *A61L 2209/14* (2013.01); *B01D 2273/30* (2013.01); *B01D 2279/65* (2013.01)

(56) References Cited

U.S. PATENT DOCUMENTS

| | | | | |
|---|---|---|---|---|
| 5,709,419 | A * | 1/1998 | Roskey | F03D 9/257 |
| | | | | 415/905 |
| 10,798,965 | B2 * | 10/2020 | Richmond | A24D 3/10 |
| 11,047,360 | B1 | 6/2021 | Houchens et al. | |
| 12,134,054 | B2 * | 11/2024 | Lucas | B01D 46/0015 |
| 2001/0015557 | A1 * | 8/2001 | Roskey | F03D 1/0608 |
| | | | | 290/55 |
| 2004/0050183 | A1 * | 3/2004 | Schimmoller | G01N 1/2273 |
| | | | | 73/863.23 |
| 2006/0123928 | A1 * | 6/2006 | Schimmoller | G01N 1/2273 |
| | | | | 73/863.23 |
| 2009/0180939 | A1 * | 7/2009 | Hagen | F23R 3/28 |
| | | | | 422/600 |
| 2011/0103953 | A1 * | 5/2011 | Haans | F03D 80/55 |
| | | | | 29/889.7 |
| 2011/0316279 | A1 * | 12/2011 | Bahari | F03D 1/04 |
| | | | | 290/55 |
| 2018/0085699 | A1 * | 3/2018 | Birtok-Baneasa | B01D 45/14 |
| 2019/0174818 | A1 * | 6/2019 | Richmond | A24D 3/163 |
| 2021/0047995 | A1 * | 2/2021 | Maris | G01M 9/065 |
| 2021/0156569 | A1 * | 5/2021 | Shingler | B03C 3/08 |
| 2023/0061818 | A1 * | 3/2023 | Westergaard | F03D 3/005 |
| 2023/0193765 | A1 * | 6/2023 | Kotay | F01D 5/187 |
| | | | | 416/95 |
| 2024/0151421 | A1 * | 5/2024 | Mou | F24F 8/108 |

OTHER PUBLICATIONS

Krath et al., Multivariate Design and Optimization of the AeroMINE Internal Turbine Blade, AIAA Propulsion and Energy Forum, Aug. 9-11, 2021.

Yang et al., Enhancing Safety of Students with Mobile Air Filtration during School Reopening from COVID-19, 2021 IEEE International Conference on Robotics and Automation (ICRA 2021) May 31-Jun. 4, 2021, Xi'an, China.

Houchens et al., A Novel Energy-conversion Device for Wind and Hydrokinetic Applications, Proceedings of the ASME-JSME-KSME 2019, 8th Joint Fluids Engineering Conference, AJKFluids2019, Jul. 28-Aug. 1, 2019, San Francisco, CA.

* cited by examiner

BERNOULLI AIR PROCESSING SYSTEM

CROSS-REFERENCE TO RELATED APPLICATIONS

The present patent application is related to and claims the priority benefit of U.S. Provisional Patent Application Ser. No. 63/091,860, filed 14 Oct. 2020, entitled BERNOULLI AIR PROCESSING SYSTEM, the contents of which are hereby incorporated by reference in its entirety into the present disclosure.

STATEMENT REGARDING GOVERNMENT FUNDING

None.

TECHNICAL FIELD

The present disclosure generally relates to an air filtration system, and in particular, to an air filtration system operating on Bernoulli's principle.

BACKGROUND

This section introduces aspects that may help facilitate a better understanding of the disclosure. Accordingly, these statements are to be read in this light and are not to be understood as admissions about what is or is not prior art.

The novel Coronavirus (SARS-CoV-2) resulted in a global pandemic in 2020. It is a highly contagious respiratory virus with significant morbidity and long-term health impacts and consequences for those who contract the virus. As of Aug. 24, 2020, more than 800,000 people have died globally. Following announcements from the World Health Organization (WHO), evidence supports airborne and droplet transmission of the virus (COVID-19) via small aerosolized droplets dispersed by sneezing, coughing and talking. VIPs—including the Prime Minister of UK and the President of the U.S.—have not been spared from the virus despite significant measures to implement precautions. Aerosolized SARS-CoV-2 coronavirus droplets range in size from 0.1 to 8 µm, and can survive in the ambient environment for a significant duration, e.g., two days. The varying droplet sizes deposited throughout the human respiratory system carry the potential to remain active and infectious. Larger particles (>50 µm) settle on the ground immediately, medium-sized particles (10-50 µm) settle within minutes and small particles (<10 µm) can remain airborne for hours and can easily be inhaled into the respiratory tract. Additionally, this new virus stays on surfaces about 3 days, bringing significant challenges in preventing further spread throughout the community, including medical personnel.

Because this novel Coronavirus is an airborne virus, many have taken measures to filter and clean ambient air in enclosed areas. In order to mitigate the spread of the virus—especially in public and crowded indoor places such as hospitals, schools, airports, etc. —a sanitization routine is needed that can successfully filter and clean the air free of these particles. Disinfection staff are exposed to both irritative disinfectants and the contaminated areas, subjecting them to increased risks for health concerns. Additionally, manual air disinfection within an enclosed area is not practical and further puts staff at risk. For example, many have used ultraviolet (UV) lights known to break down these viral particles in an indiscriminate manner in large and small areas (e.g., hotel rooms, surgical suites). However, UV radiation damages exposed skin cells and can degrade other materials such as plastics resulting in the premature failure of electronics and other commonly used items.

Therefore, there is an unmet need for a novel approach to filter and clean air containing virus particles that is safe for both humans and other objects in an enclosed area.

SUMMARY

An air intake module is disclosed. The module includes a manifold. The module further includes a first airfoil disposed on the manifold and configured to allow air of an area designed to have its air cleaned to enter the manifold. Additionally, the module includes a second airfoil disposed one the manifold opposite the first airfoil configured to allow air from the area to enter the manifold. Furthermore, the module includes a collector provided in between the first airfoil and the second airfoil and disposed on the manifold configured to receive air from the manifold and thus filter the air.

An air processing system is disclosed. The system includes a mobile robot. The robot includes an intake module. The module includes a manifold. The module further includes a first airfoil disposed on the manifold and configured to allow air of an area designed to have its air cleaned to enter the manifold. Additionally, the module includes a second airfoil disposed one the manifold opposite the first airfoil configured to allow air from the area to enter the manifold. Furthermore, the module includes a collector provided in between the first airfoil and the second airfoil and disposed on the manifold configured to receive air from the manifold and thus filter the air. The system further includes a controller configured to provide one of remote control and autonomous control of the mobile robot.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure, the term "about" can allow for a degree of variability in a value or range, for example, within 10%, within 5%, or within 1% of a stated value or of a stated limit of a range.

In the present disclosure, the term "substantially" can allow for a degree of variability in a value or range, for example, within 90%, within 95%, or within 99% of a stated value or of a stated limit of a range.

Figure 1:
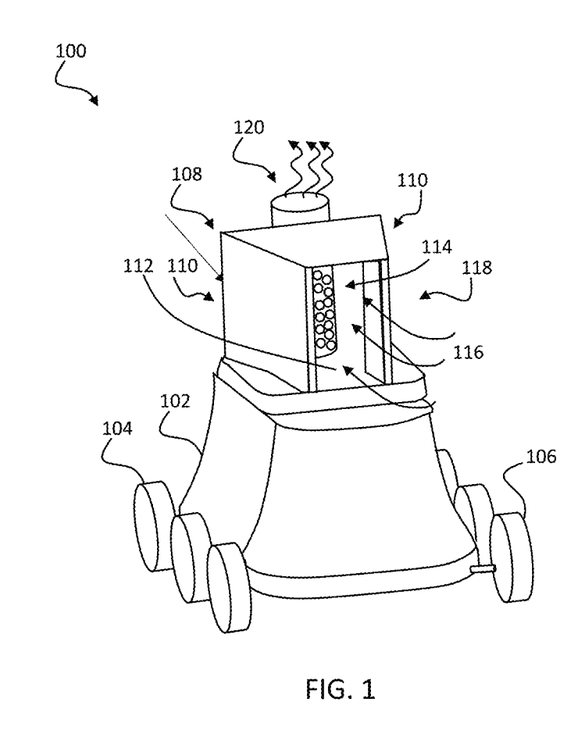
FIG. 1 is a perspective view of a Bernoulli robot that is used as a mobile air processing system.

A novel approach to process air containing virus particles that is safe for both humans and other objects in an enclosed area is presented. Towards this end, a robot that is either remotely controlled or which is autonomous is described in the present disclosure. The robot of the present disclosure is also referred to herein as the Bernoulli's Robot, owing to an air intake apparatus that is designed to selectively maximize air intake into a manifold of the robot. Referring to FIG. 1, a perspective view of the Bernoulli's Robot 100 is provided. The Bernoulli Robot 100 includes a base 102 which provide propulsion for the robot 100 via a set of propulsion wheels 104 as well as steering wheels 106. The steering wheels 106 can also be propulsion type, and similarly the propulsion wheels 104 can also be the steering type. The robot 100 also includes a top 108. The top 108 includes two moveable airfoils 110 that can selectively allow air to enter the top 108. These two moveable airfoils 110 are designed to selectively enlarge the frontal area of the robot in order to admit more air through an intake manifold 112. Each of the two moveable airfoils 110 are shaped similar to a wing of an airplane and can articulate each about a central axis to vary the frontal area of the intake manifold 112. The airfoils according to one embodiment include smooth surfaces and according to another embodiment include perforation as discussed below for enhancement of air intake. Towards the back end of the intake manifold 112 is a perforated cylinder (also referred to herein as the center body or the collector or the perforated collector 114) whereby intake air is processed for filtration. Together the two moveable airfoils form an air inlet 116. Once air enters the inlet 116, and is received by the perforated collector and processed as discussed below, air is allowed to exit via an outlet. The outlet in one embodiment as shown in FIG. 1 includes a turbo fan module 120.

The two moveable airfoils 110 and the perforated collector 114 constitute a novel Bernoulli air intake module 118. The Bernoulli air intake module 118 is designed to increase the efficiency of air filtration by the help of the movement of the Bernoulli air intake module 118 itself, in particular by way of articulation of the two moveable airfoils 110. This Bernoulli air intake module 118 can be installed on top of a mobile cleaning-robot as shown in FIG. 1 to filter ambient air from contaminants present therein. The unique design of the Bernoulli air intake module 118 increases the air swept area as the air intake module moves through the air to trap the contaminants, thereby it is ideal for a robotic disinfection application.

Figure 2A:
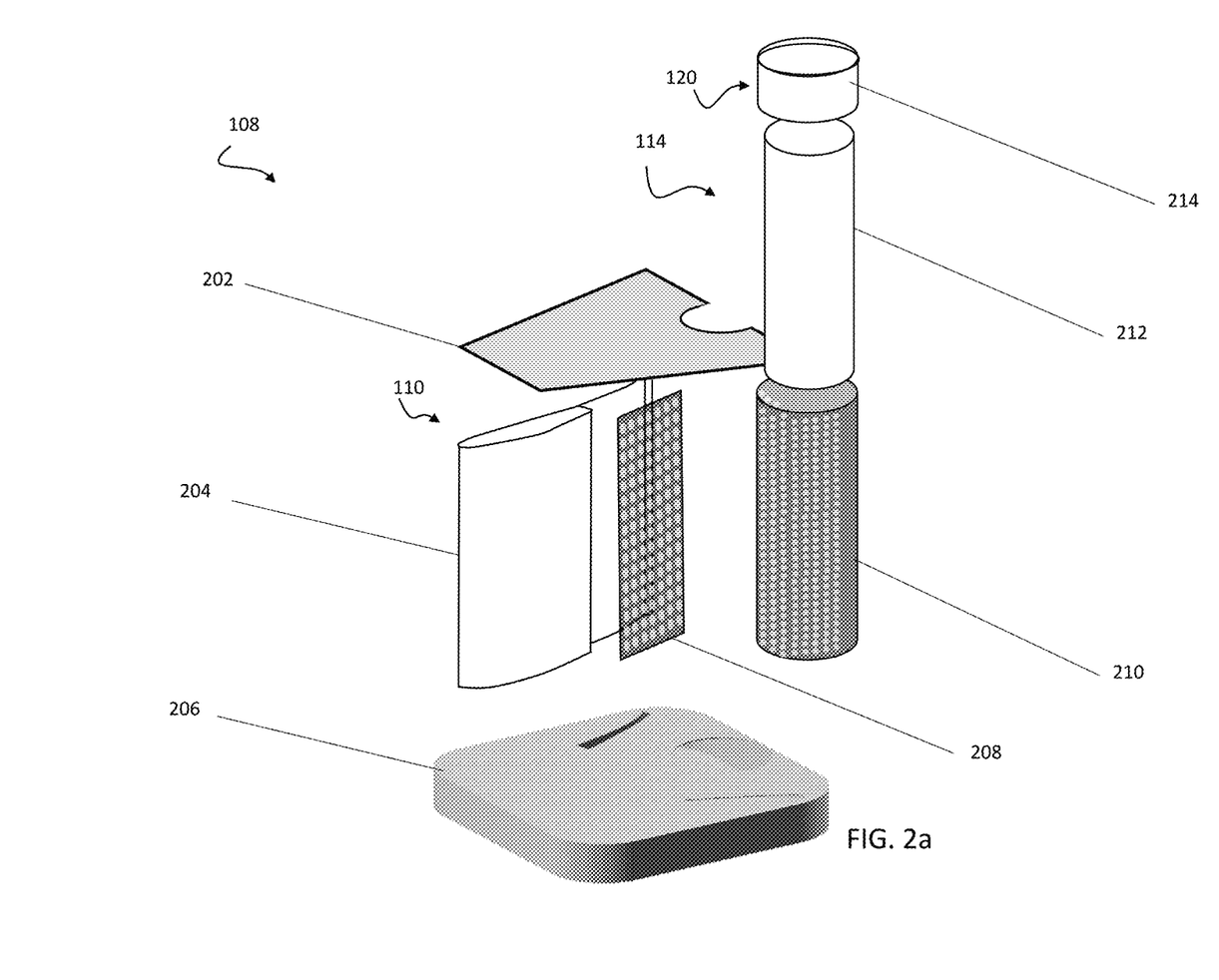
FIG. 2a is an exploded perspective view of a moveable airfoil and a perforated collector which constitute various parts of the Bernoulli robot of FIG. 1.

Referring to in FIGS. 2a, 2b, 2c, 2d, 2e, 2f, and 2g various views of the moveable airfoils 110 and the perforated collector 114 are provided. In particular, referring to FIG. 2a, an exploded perspective view of one moveable airfoil 110 and the perforated collector 114 is provided. Shown in FIG. 2a are also a top plate 202 which allows securement of the perforated collector 114 as well as proper directional flow of air into the air intake module. The perforated collector 114 is also shown in an exploded view in FIG. 2a, depicting a center body with perforation 210, an inner duct 212 adapted to allow flow of air into a manifold 206 disposed at the base of the perforated collector 114, and the turbo fan module 120 containing a motor assembly 214 which includes a turbo fan, and optionally a muffler. The moveable airfoil 110 includes an airfoil 204 and may also optionally include a perforated foil 208 adapted to enhance air flow into the air intake module. Air movement within the air intake module is further described below.

Figure 2B:
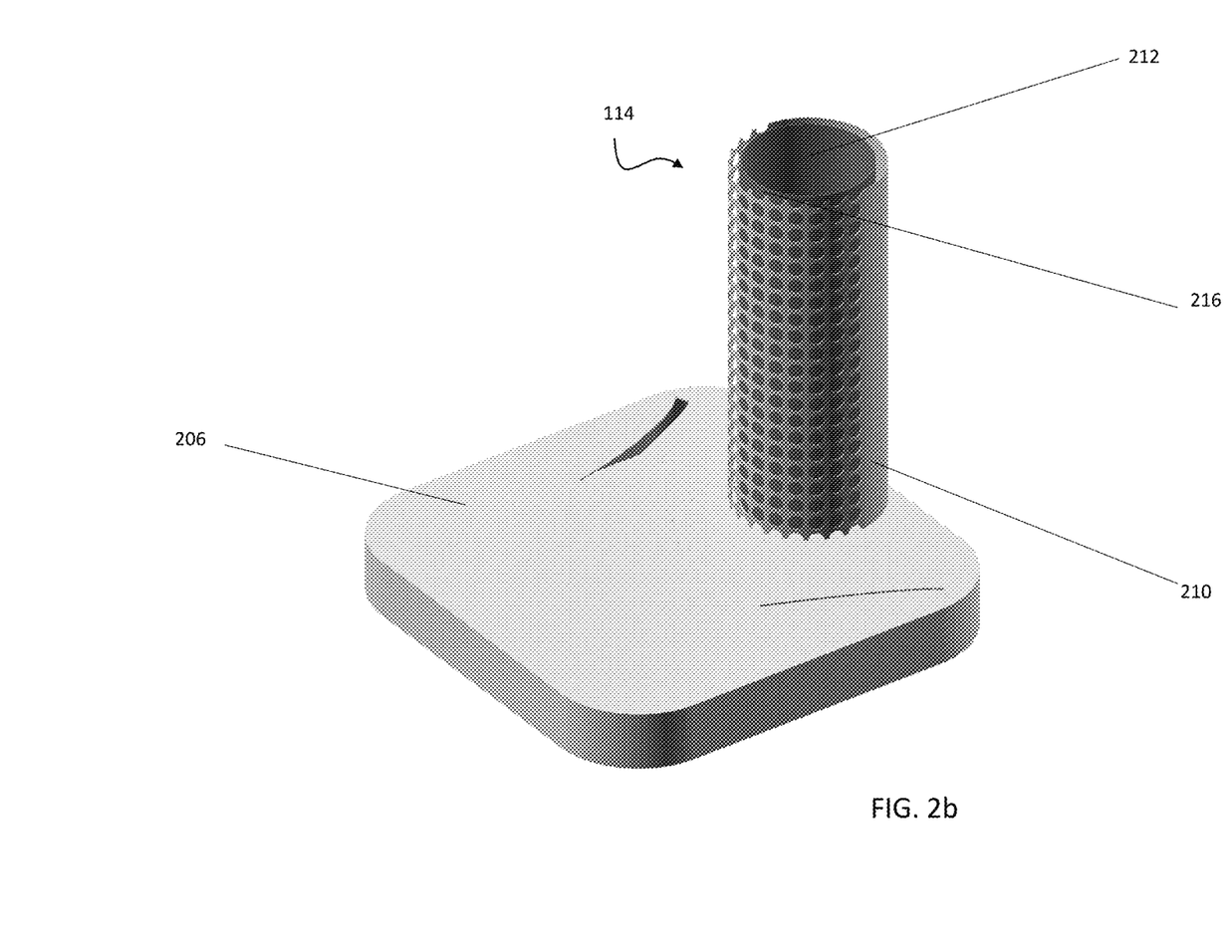
FIG. 2b is a perspective view of the perforated collector shown being mounted on a manifold which also constitutes a component of the Bernoulli robot of FIG. 1.

Referring to FIG. 2b, a perspective view of the perforated collector 114 is shown being mounted on the manifold 206. Air enters through the center body with perforation 210 and is directed into the manifold 206 via an annulus 216 between the center body with perforation 210 and the inner duct 212.

Figure 2C:
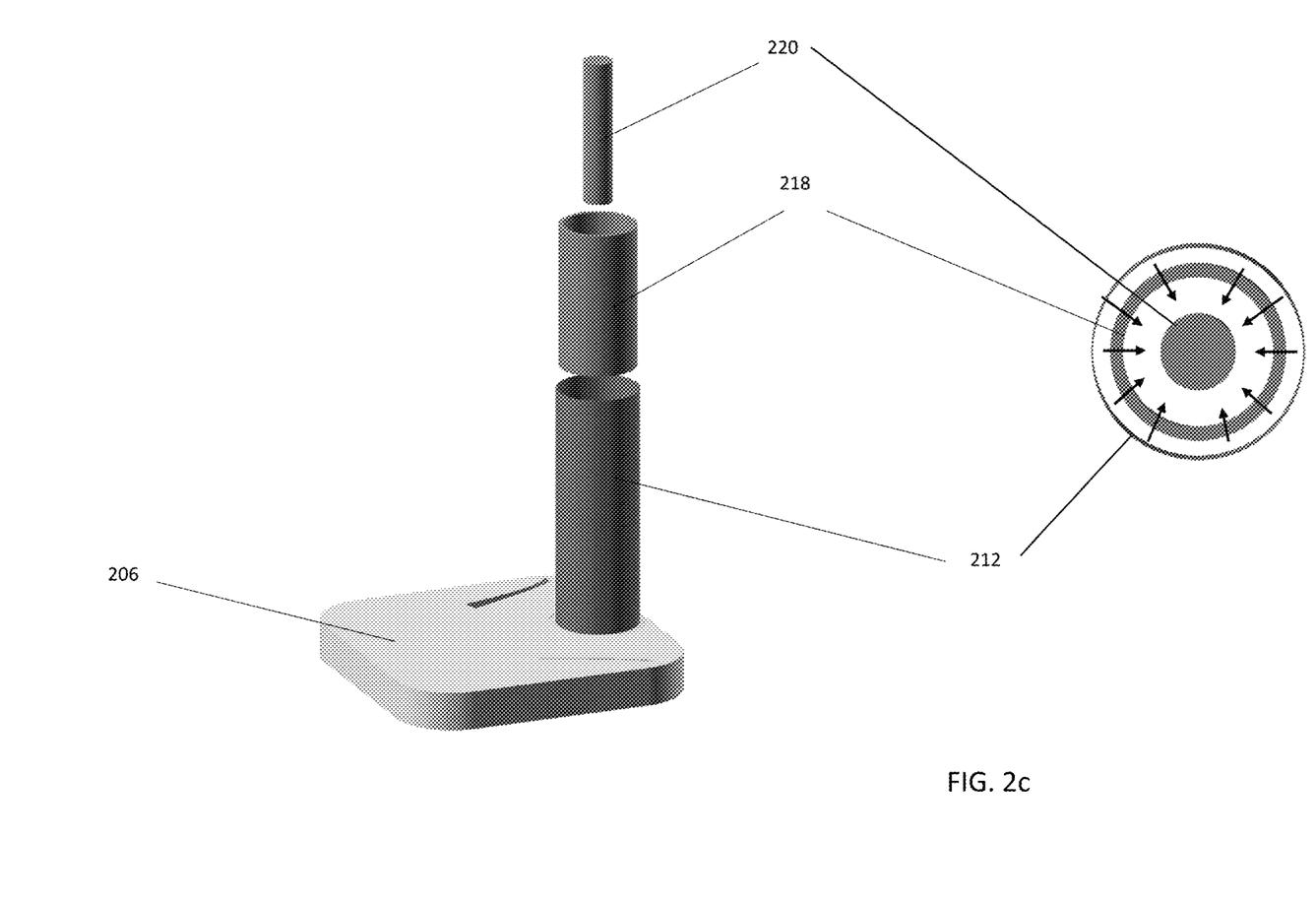
FIG. 2c is an exploded view of the center body of the perforated collector, according to one embodiment, showing the associated air processing.

Referring to FIG. 2c, an exploded view of the center body of the perforated collector 114 is shown, according to one embodiment, showing the associated air processing. The inner duct 212 is sealingly coupled to the manifold 206 such that all air that had moved into the manifold is forced to only come out of the inner duct 212. Air on its way out of the manifold 206 is forced to enter a radial filter 218 as air travels through the annulus 216 which is formed between the inner duct 212 and the radial filter 218. The radial filter 218 may be a passive or a smart filter similar to that described in the U.S. Pub. App. Nos. 20100313748 and 20190083917. The radial filter 218 retains particles of various sizes and thus filters the incoming air free from those particles. While in the filter, the air is subjected to an optional UV source 220 adapted to inactivate the infectious or adverse particles captured in the filter as well as the particles that are too small that may pass through the radial filter 218. The UV source 220 may be a UV lamp that is cylindrically shaped and is adapted to fit inside the radial filter 218. Thus, the airflow from the manifold 206 passes through the annulus 216, then through the radial filter 218 and out the turbo fan module 120.

Figure 2D:
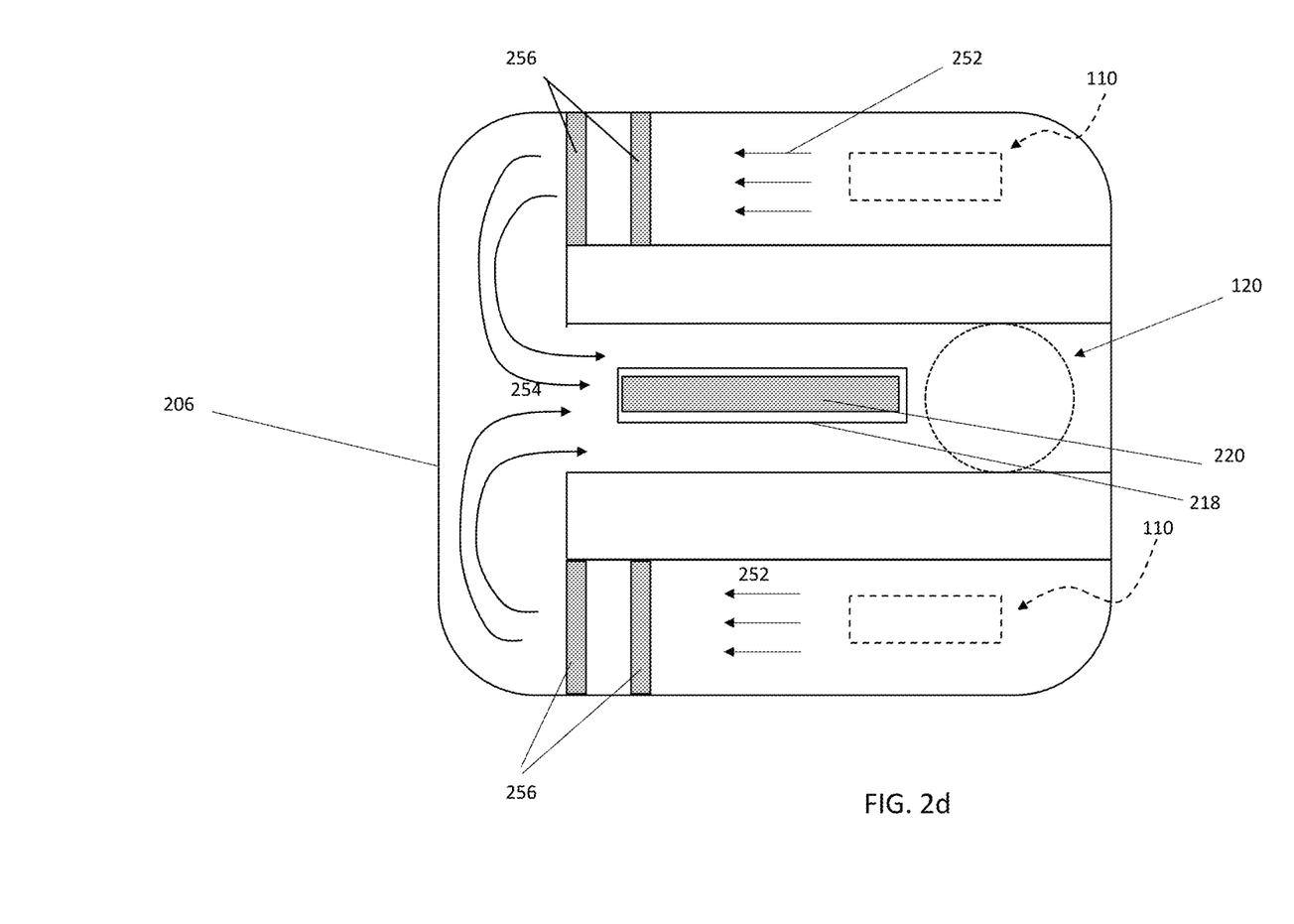
FIG. 2d is a schematic depicting the airflow through the manifold.

Referring to FIG. 2d, a schematic is shown depicting the airflow through the manifold 206. As shown, the air is brought into the manifold 206 through perforations of the moveable airfoils 110 as shown by the arrows 252. As air enters into the manifold 206, it passes through an optional filter systems 256 that can be a passive filter or a smart filter, as discussed above with respect to the radial filter 218. Air, as shown by air flow arrows 254 then enters the annulus 216 and is allowed to pass through the radial filter 218 being exposed to the optional UV source 220 and exits through the turbo fan module 120, as described above.

Figure 2E:
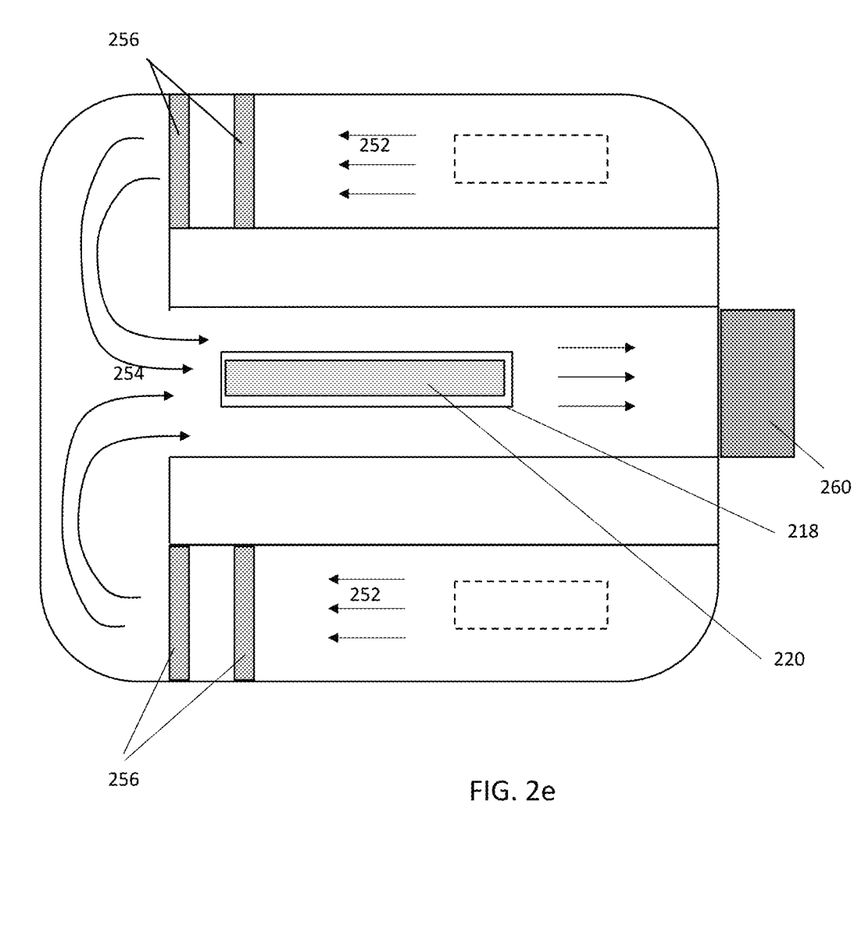
FIG. 2e is another schematic similar as that shown in FIG. 2d but with a change in a turbo fan module, according to an embodiment of the present disclosure.

Referring to FIG. 2e, the same schematic as that shown in FIG. 2d is shown but with a change in the turbo fan module 120, according to another embodiment. In this embodiment, a turbo fan 260 is integrated into the perforated collector 114.

Figure 2F:
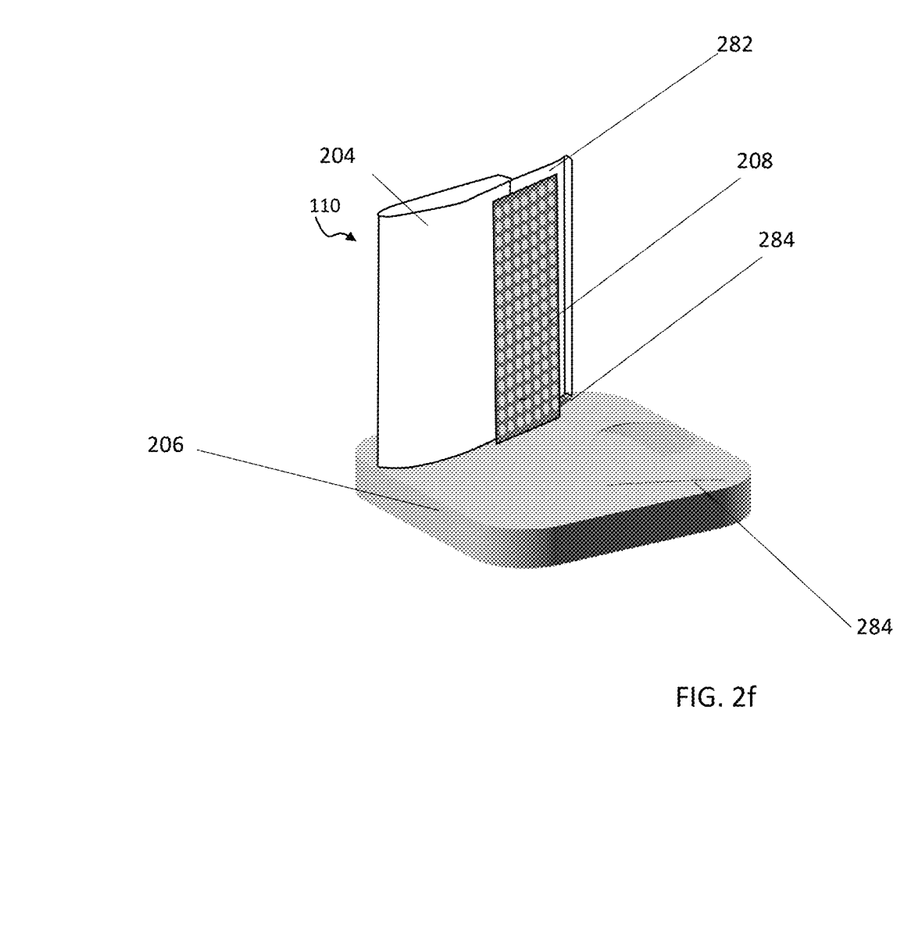
FIG. 2f is a perspective view of various components of the Bernoulli robot of FIG. 1, wherein air intakes through channels (right side and left side) between the moveable airfoils and the manifold are shown.

Referring to FIG. 2f, air intake through channels 284 (right side and left side) between the moveable airfoils 110 and the manifold 206 are shown. In one case, the airfoils include perforated foils 208 for improved air flow into said openings via a space between the perforated foils 208 and airfoil flaps 282 which is part of the moveable airfoils 110.

Specifically, the channels 284 at the manifold are at a negative pressure, thus actively drawing in air, owing to the air flow through the turbo fan module 120.

Figure 2G:
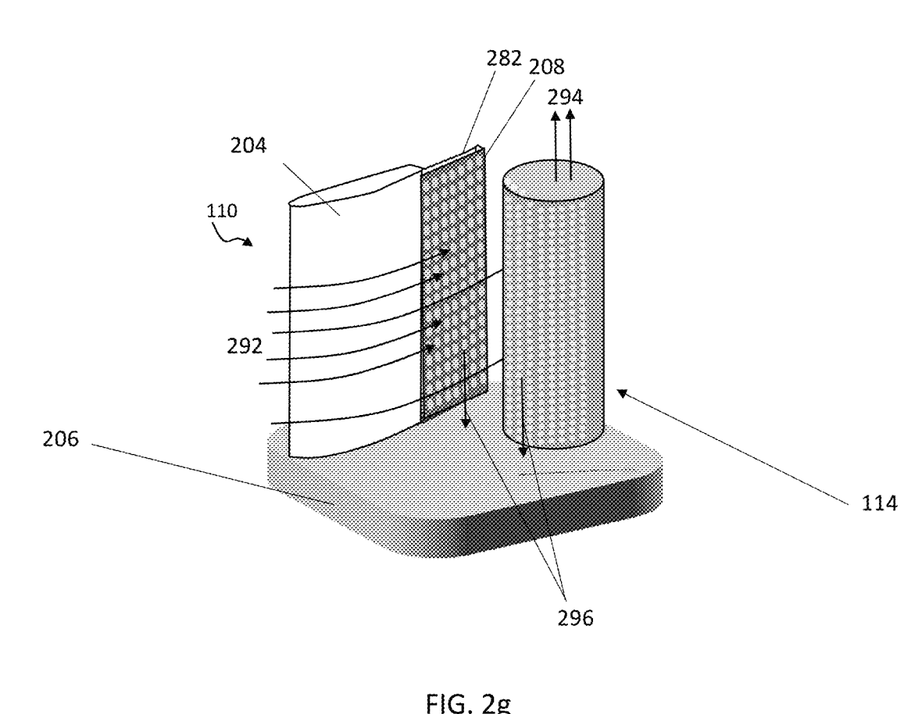
FIG. 2g is a perspective view of various components of the Bernoulli robot of FIG. 1, wherein air movement about the moveable airfoil (with the optional perforated foils) is shown in addition to the perforated collector including its perforations.
Figure 3A:
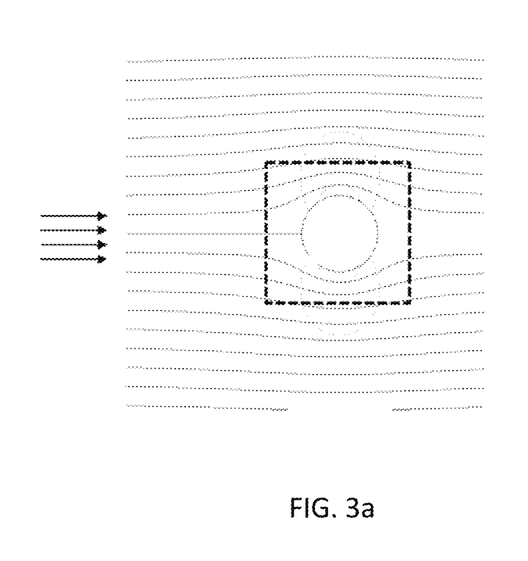
FIG. 3a is a schematic showing air intake without the airfoils.
Figure 3B:
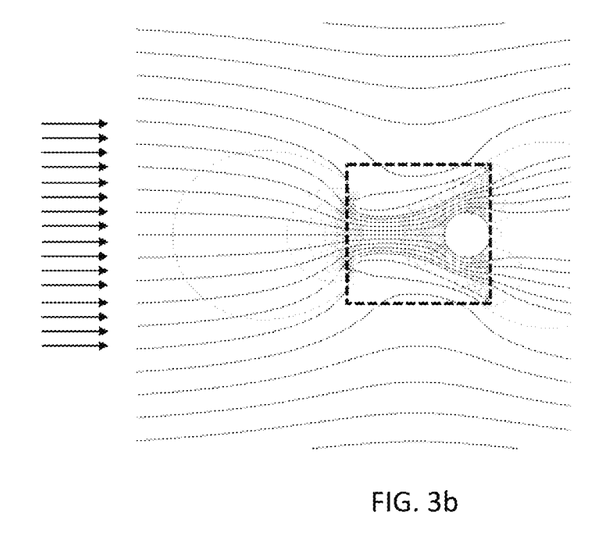
FIG. 3b, is another schematic showing air intake similar to FIG. 3a, however, in this figure the air movement is shown with airfoils.
Figure 4:
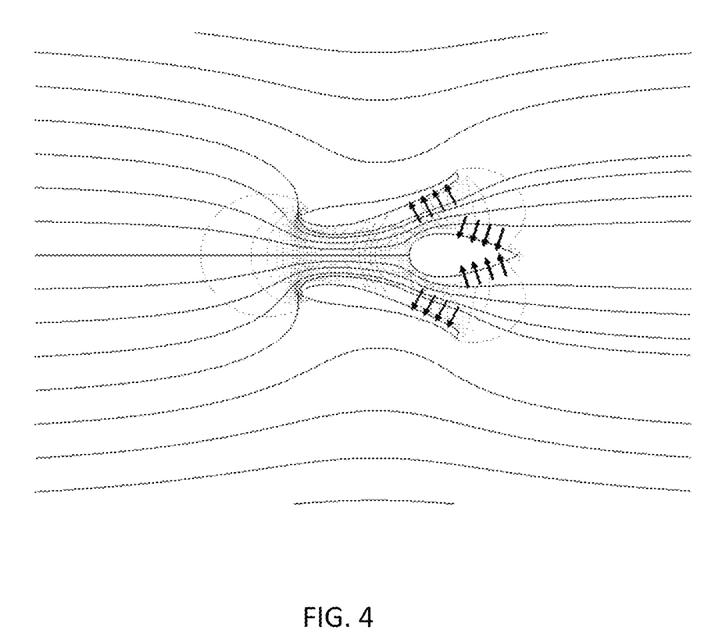
FIG. 4 is another schematic showing air movement in the perforated collector shaped as an airfoil.

Referring to FIG. 2g, a perspective view of the moveable airfoils 110 (with the optional perforated foils 208) is shown in addition to the perforated collector 114 including its perforations. Air passing by the moveable airfoils 110 (shown as arrows 292) is pulled into the manifold 206 via channels 284 (as shown by arrows 296) between the moveable airfoils 110 and the manifold 206 and then through the annulus (not shown) and then to the turbo fan module 120 (as shown by arrows 294).

As discussed above, infectious bioaerosol droplet sizes range in order of microns, which can remain suspended in the ambient environment for several hours and can be inhaled and infect humans. Hospitals, public places and more crowded confined spaces need bioaerosol filtration systems to ensure safety of the people present, making air filtration systems more relevant than ever in the recent viral pandemic.

The novel Bernoulli robot 100 shown in FIG. 1, increases the efficiency of the air filtration system, when the system is moving in space by leveraging the air movement relative to the system. Towards this end, two moveable airfoils 110 are placed at the sides of a perforated collector 114 (see FIG. 1 or 2) that draws the air inside the manifold 206 and through the perforated collector 114 and through the turbo fan module 120. In FIGS. 1 and 2, the perforated collector 114 is cylindrically shaped, however, as discussed with respect to FIG. 4, the collector can be shaped differently, e.g., the shape of an airfoil. Named after Bernoulli's principle from fluid mechanics, the Bernoulli robot 100 creates a low-pressure region, which acts as an intake between the moveable airfoils 110 and the manifold 206, effectively converting the energy in the moving air to create suction of the air toward the radial air filter 218 inside the perforated collector 114 of the robot 100 (See FIG. 2). The angle of the moveable airfoils 110 can be independently changed via one or two servo motors or other actuators (not shown) connected to each moveable airfoil 110. The motion of the moveable airfoils 110 can in some cases be dynamically adjusted as the robot base maneuvers, for example passing sharp corners, where asymmetric air intake may be needed by adjusting one moveable airfoil's 110 angle with respect to the other moveable airfoil's 110 angle.

The size and height of the moveable airfoils 110 can be chosen relative to the air filtration capacity that is required by the robot 100 depending on the use case in different environments or desired sweeping heights.

Since velocity of the robot 100 is relatively small (e.g., 0.2 m/s to 1 m/s) compared to normal operations of moveable airfoils 110, the suction of the air over the airfoils 204 of the moveable airfoils 110 are designed to stabilize and enhance the performance (lift capabilities) of the moveable airfoils 110 through the boundary layer suction. The higher the lift that can be achieved on the airfoils 204, the larger an area can be swept in each pass. This phenomenon is shown in FIGS. 3*a* and 3*b*, where air intake is shown without the airfoils in FIG. 3*a*, as compared to with airfoils 204 in FIG. 3*b*. The smaller number of arrows in FIG. 3*a* show a smaller amount of air intake as compared to FIG. 3*b* with shows a large amount of air intake. The more effective the airfoils are, the larger the area is swept. Contrast this novel arrangement to a body, such as a cylinder, sweeping an area smaller or equal to its cross section, which is shown in FIG. 3*a*.

While a cylindrically shaped object is shown in the perforated collector 114, no such limitation is intended. Another example of a perforated body to receive air from the manifold 206 is shown in FIG. 4. Curved lines indicate contours of pressure, while arrowed lines indicate streamlines. The arrows indicate the boundary layer suction and air intake for both the two moveable airfoils 110 and the center body being another airfoil (the alternate shape of the perforated collector 114). In this embodiment, the perforated collector having either a cylindrical shape or other shapes primarily prevents airflow on the centerline between the two airfoils to escape filtration. The center body can be a cylinder shape similar to the discussion above with respect to the perforated collector 114, which simplifies construction and makes it practical to insert cylindrical filtration system in the internals of the tube. However, the center could also be airfoil shaped, as shown in FIG. 4. This arrangement is more complex to manufacturer, however benefits in further efficiency gains and reduction of the wake disturbance the robot makes as it moves through the air.

A fan (not shown) may be added to the perforated collector 114 to assist in drawing the air by creating an active suction at the manifold 206. The speed of the fan may be adjusted as the Bernoulli robot 100 requires more or less air intake depending on the situation. For example, as the Bernoulli robot 100 is maneuvering around a corner, the speed of the fan and the angle of the moveable airfoils 110 need to be adjusted in concert with one-another to avoid turbulence at the channels 284. These variables can also be controlled in concert with the speed and directionality of the robot 100. Towards this end, the Bernoulli robot 100 can be equipped with i) a vision system (not shown); and/or ii) a sonar system (not shown) that can interrogate surrounding of the robot to determine location of the robot in a room. Speed and directionality of the robot 100 can be modified to effectuate proper air intake as well as proper sweeping around an enclosed area.

While not shown, each of the perforations of the perforated foil 208 of the two moveable airfoils 110 or the perforation of the center body with perforation 210 of the perforated collector 114 can be equipped with a passive or a smart filter (as discussed with respect to the radial filter 218) to further remove particles of predetermined size from incoming air.

A Bernoulli controller 1000 is adapted to control the actuators of the moveable airfoils 110, the optional UV source 220, the vision system (not shown), and/or the sonar system (not shown). Referring to FIG. 5, an example of the controller 1000 is provided that can interface with the above-discussed elements of the robot 100. Referring to FIG. 5, a high-level diagram showing the components of an exemplary data-processing system 1000 (also referred herein as Bernoulli controller) for analyzing data and performing other analyses described herein, and related components. The system includes a processor 1086, a peripheral system 1020, a user interface system 1030, and a data storage system 1040. The peripheral system 1020, the user interface system 1030 and the data storage system 1040 are communicatively connected to the processor 1086. Processor 1086 can be communicatively connected to network 1050 (shown in phantom), e.g., the Internet or a leased line, as discussed below. The imaging described in the present disclosure may be obtained using imaging sensors 1021 and/or displayed using display units (included in user interface system 1030) which can each include one or more of systems 1086, 1020, 1030, 1040, and can each connect to one or more network(s) 1050. Processor 1086, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Figure 5:
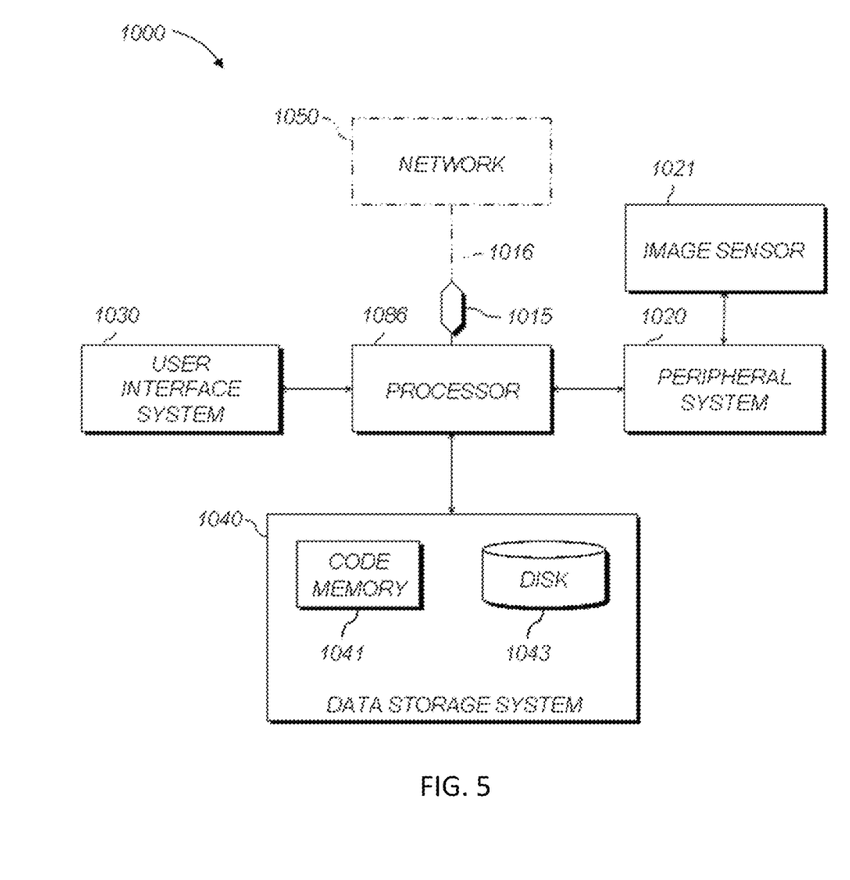
FIG. 5 is a schematic of a controller that is adapted to control the Bernoulli robot of the present disclosure.

Processor 1086 can implement processes of various aspects described herein. Processor 1086 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise. Processor 1086 can include Harvard-architecture components, modified-Harvard-architecture components, or Von-Neumann-architecture components.

The phrase "communicatively connected" includes any type of connection, wired or wireless, for communicating data between devices or processors. These devices or processors can be located in physical proximity or not. For example, subsystems such as peripheral system 1020, user interface system 1030, and data storage system 1040 are shown separately from the data processing system 1086 but can be stored completely or partially within the data processing system 1086.

The peripheral system 1020 can include one or more devices configured to provide digital content records to the processor 1086. For example, the peripheral system 1020 can include digital still cameras, digital video cameras, cellular phones, or other data processors. The processor 1086, upon receipt of digital content records from a device in the peripheral system 1020, can store such digital content records in the data storage system 1040.

The user interface system 1030 can include a mouse, a keyboard, another computer (connected, e.g., via a network or a null-modem cable), or any device or combination of devices from which data is input to the processor 1086. The user interface system 1030 also can include a display device, a processor-accessible memory, or any device or combination of devices to which data is output by the processor 1086. The user interface system 1030 and the data storage system 1040 can share a processor-accessible memory.

In various aspects, processor 1086 includes or is connected to communication interface 1015 that is coupled via network link 1016 (shown in phantom) to network 1050. For example, communication interface 1015 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WiFi or GSM. Communication interface 1015 sends and receives electrical, electromagnetic or optical signals that carry digital or analog data streams representing various types of information across network link 1016 to network 1050. Network link 1016 can be connected to network 1050 via a switch, gateway, hub, router, or other networking device.

Processor 1086 can send messages and receive data, including program code, through network 1050, network link 1016 and communication interface 1015. For example, a server can store requested code for an application program (e.g., a JAVA applet) on a tangible non-volatile computer-readable medium to which it is connected. The server can retrieve the code from the medium and transmit it through network 1050 to communication interface 1015. The received code can be executed by processor 1086 as it is received, or stored in data storage system 1040 for later execution.

Data storage system 1040 can include or be communicatively connected with one or more processor-accessible memories configured to store information. The memories can be, e.g., within a chassis or as parts of a distributed system. The phrase "processor-accessible memory" is intended to include any data storage device to or from which processor 1086 can transfer data (using appropriate components of peripheral system 1020), whether volatile or non-volatile; removable or fixed; electronic, magnetic, optical, chemical, mechanical, or otherwise. Exemplary processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 1040 can be a tangible non-transitory computer-readable storage medium, i.e., a non-transitory device or article of manufacture that participates in storing instructions that can be provided to processor 1086 for execution.

In an example, data storage system 1040 includes code memory 1041, e.g., a RAM, and disk 1043, e.g., a tangible computer-readable rotational storage device such as a hard drive. Computer program instructions are read into code memory 1041 from disk 1043. Processor 1086 then executes one or more sequences of the computer program instructions loaded into code memory 1041, as a result performing process steps described herein. In this way, processor 1086 carries out a computer implemented process. For example, steps of methods described herein, blocks of the flowchart illustrations or block diagrams herein, and combinations of those, can be implemented by computer program instructions. Code memory 1041 can also store data, or can store only code.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects. These aspects can all generally be referred to herein as a "service," "circuit," "circuitry," "module," or "system."

Furthermore, various aspects herein may be embodied as computer program products including computer readable program code stored on a tangible non-transitory computer readable medium. Such a medium can be manufactured as is conventional for such articles, e.g., by pressing a CD-ROM. The program code includes computer program instructions that can be loaded into processor 1086 (and possibly also other processors), to cause functions, acts, or operational steps of various aspects herein to be performed by the processor 1086 (or other processors). Computer program code for carrying out operations for various aspects described herein may be written in any combination of one or more programming language(s), and can be loaded from disk 1043 into code memory 1041 for execution. The program code may execute, e.g., entirely on processor 1086, partly on processor 1086 and partly on a remote computer connected to network 1050, or entirely on the remote computer.

Those having ordinary skill in the art will recognize that numerous modifications can be made to the specific implementations described above. The implementations should not be limited to the particular limitations described. Other implementations may be possible.

The invention claimed is:

1. An air intake module, comprising:
   a manifold;
   a first airfoil disposed on the manifold and configured to allow air of an area designed to have its air cleaned to enter the manifold;
   a second airfoil disposed on the manifold opposite the first airfoil configured to allow air from the area to enter the manifold; and
   a collector provided in between the first airfoil and the second airfoil and disposed on the manifold configured to receive air from the manifold and thus filter the air.

2. The air intake module of claim 1, the first airfoil is coupled to a first actuator, configured to be articulated about a first axis.

3. The air intake module of claim 2, the second airfoil is coupled to a second actuator, configured to be articulated about a second axis.

4. The air intake module of claim 1, the first airfoil includes a smooth surface.

5. The air intake module of claim 1, the first airfoil includes a perforated surface configured to improve air flow into the manifold.

6. The air intake module of claim 1, the second airfoil includes a smooth surface.

7. The air intake module of claim 1, the second airfoil includes a perforated surface configured to improve air flow into the manifold.

8. The air intake module of claim 1, wherein the collector has a cylindrical cross section, and wherein the collector includes a perforated surface to improve air movement therein.

9. The air intake module of claim 1, wherein the collector has an airfoil cross section configured to improve air movement.

10. The air intake module of claim 1, the first airfoil includes a perforated surface configured to improve air flow into the manifold, and the perforated surface of the first airfoil includes a first filter; the second airfoil includes a perforated surface configured to improve air flow into the manifold and the perforated surface of the second airfoil includes a second filter; and the collector includes a perforated surface to improve air movement therein and the perforated surface of the collector includes a third filter.

11. An air processing system, comprising:
    a mobile robot comprising an intake module, the intake module comprising:
      a manifold;
      a first airfoil disposed on the manifold configured to allow air of an area designed to have its air cleaned to enter the manifold;
      a second airfoil disposed on the manifold opposite the first airfoil configured to allow air of the area to enter the manifold; and
      a collector provided in between the first airfoil and the second airfoil and disposed on the manifold configured to receive air from the manifold and thus filter the air; and
    a controller configured to provide one of remote control and autonomous control of the mobile robot.

12. The air processing system of claim 11, the first airfoil is coupled to a first actuator controlled by the controller, configured to be articulated about a first axis.

13. The air processing system of claim 12, the second airfoil is coupled to a second actuator controlled by the controller, configured to be articulated about a second axis.

14. The air processing system of claim 11, the first airfoil includes a smooth surface.

15. The air processing system of claim 11, the first airfoil includes a perforated surface configured to improve air flow into the manifold.

16. The air processing system of claim 11, the second airfoil includes a smooth surface.

17. The air processing system of claim 11, the second airfoil includes a perforated surface configured to improve air flow from the manifold.

18. The air processing system of claim 11, wherein the collector has a cylindrical cross section and wherein the collector includes a perforated surface to improve air movement therein.

19. The air processing system of claim 11, wherein the collector has an airfoil cross section configured to improve air movement.

20. The air processing system of claim 11, wherein the controller is adapted to control one or more of a sonar system and an optical system configured to transmit and receive signals for steering.

21. The air processing system of claim 11, wherein the mobile robot further includes a fan module for outputting processed air, where the fan module muffles air being output from the mobile robot.

22. The air processing system of claim 11, wherein the mobile robot further includes a radial filter disposed in the collector adapted to capture particles of predetermined sizes.

23. The air processing system of claim 22, wherein the mobile robot further includes a UV source included in the collector, adapted to inactivate particles passing through the collector and particles captured in the radial filter.

24. The air processing system of claim 11, the first airfoil includes a perforated surface configured to improve air flow into the manifold, and the perforated surface of the first airfoil includes a first filter; the second airfoil includes a perforated surface configured to improve air flow into the manifold and the perforated surface of the second airfoil includes a second filter; and the collector includes a perforated surface to improve air movement therein and the perforated surface of the collector includes a third filter.

* * * * *